US006851260B2

(12) United States Patent  (10) Patent No.: US 6,851,260 B2
Mernøe  (45) Date of Patent: Feb. 8, 2005

(54) SHAPE MEMORY ALLOY ACTUATOR

(75) Inventor: Morten Mernøe, Charlottenlund (DK)

(73) Assignee: M 2 Medical A/S, Gentofte (DK)

( * ) Notice: Subject to any disclaimer, the term of this patent is extended or adjusted under 35 U.S.C. 154(b) by 0 days.

(21) Appl. No.: 10/622,065

(22) Filed: Jul. 17, 2003

(65) Prior Publication Data
US 2004/0068985 A1 Apr. 15, 2004

Related U.S. Application Data

(63) Continuation of application No. PCT/DK02/00031, filed on Jan. 16, 2002.

(51) Int. Cl.[7] .............................. F03G 7/06; F24F 13/14; H01H 71/18
(52) U.S. Cl. ...................... 60/527; 60/641.1; 60/641.6; 310/306; 337/140; 374/112; 446/14
(58) Field of Search ................................ 60/527, 641.1, 60/641.6; 310/306; 374/112; 337/123, 140; 446/14

(56) References Cited

U.S. PATENT DOCUMENTS

| 4,191,053 | A | * | 3/1980 | Hart et al. | 374/112 |
|---|---|---|---|---|---|
| 4,772,807 | A | * | 9/1988 | Bouvot | 60/527 |
| 4,829,843 | A | * | 5/1989 | Suzuki | 60/527 |
| 4,887,430 | A | * | 12/1989 | Kroll et al. | 60/527 |
| 5,684,448 | A | * | 11/1997 | Jacobsen et al. | 337/140 |
| 6,390,878 | B1 | * | 5/2002 | Zhou et al. | 446/14 |

FOREIGN PATENT DOCUMENTS

| JP | 60-166766 | 8/1985 |
|---|---|---|
| JP | 62-66047 | 3/1987 |
| JP | 62-131156 | 6/1987 |
| JP | 2-241989 | 9/1990 |
| JP | 2-241990 | 9/1990 |

* cited by examiner

Primary Examiner—Sheldon J Richter
(74) Attorney, Agent, or Firm—Klein, O'Neill & Singh, LLP; Howard J. Klein

(57) ABSTRACT

A shape memory alloy actuator comprising a body (1) connected through an arm (5) with an activating member (15), the body (1) being arranged for rotation around a pivot (2) and connected to a first wire (9) and a second wire (10) of a shape memory alloy such as nitinol and to a biasing means such as a tension spring (6) such that heating and therefore shortening of the wire (10) rotates the body (1) counter-clockwise such that the tension spring (6) is in its cocked position while heating (shortening) of the wire (9) and cooling (lengthening) of the wire (10) to the position shown in 10a rotates the body (1) clockwise past a balance point for the tension spring (16) whereafter the body (1) rotates further clockwise under the influence of the tension spring (6), thereby exerting a relatively powerful actuation of the activating member (15), the whole cyclus being repeated by heating wire (10) causing it to shorten and rotate the body (1) counter-clockwise until the spring (6) is cocked again.

10 Claims, 3 Drawing Sheets

Figure 1:
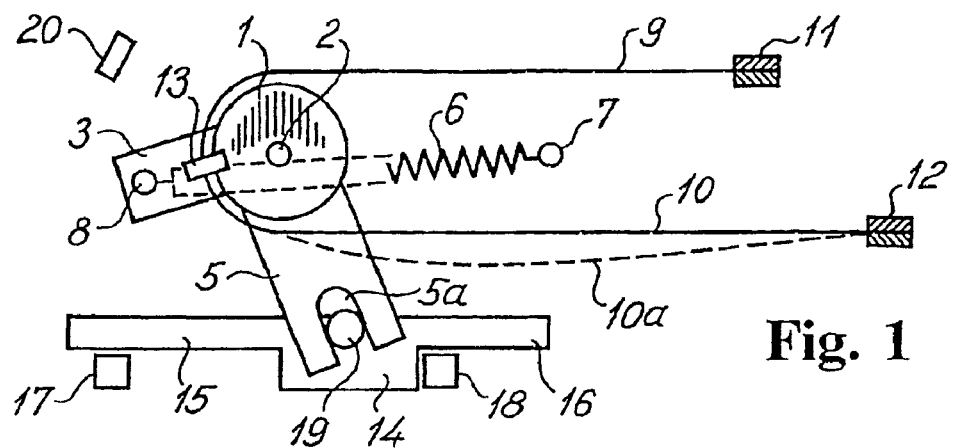

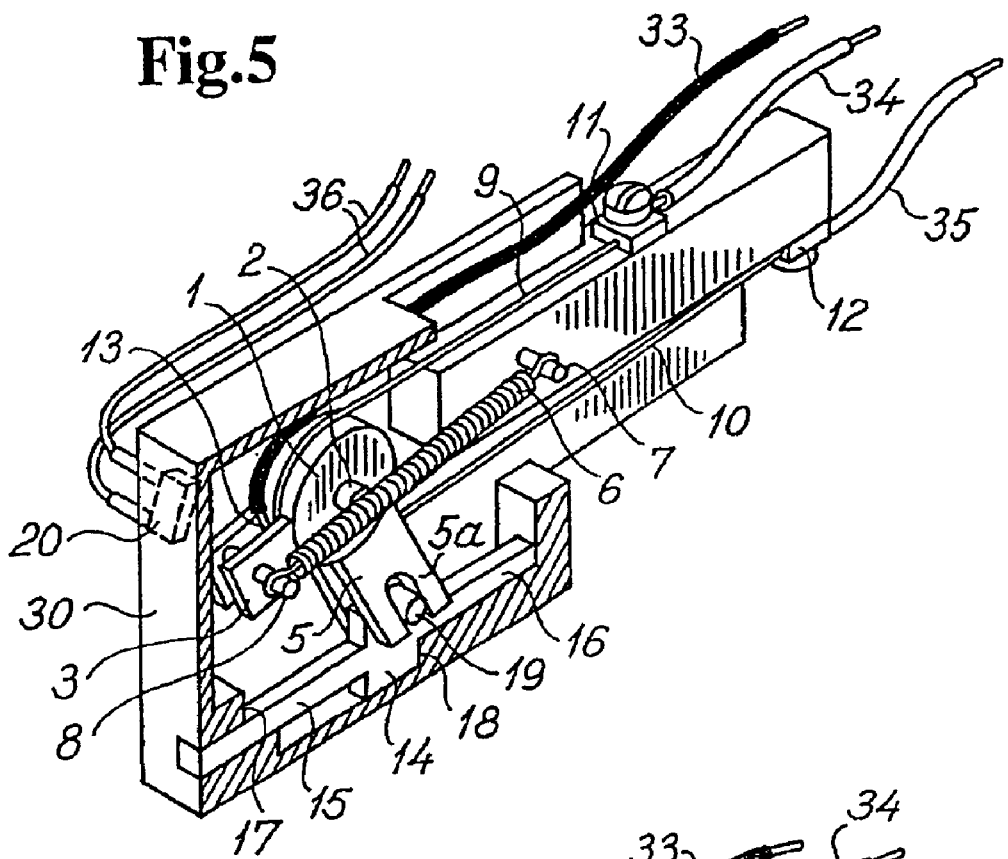
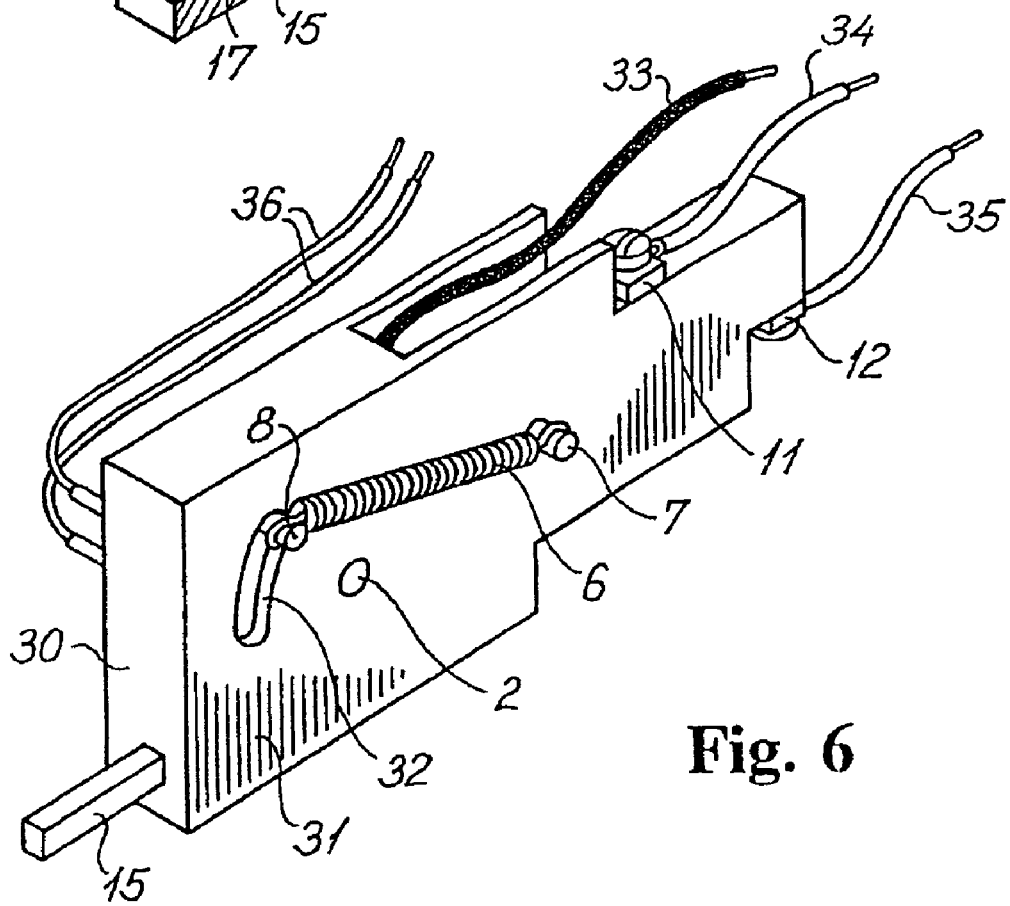

SHAPE MEMORY ALLOY ACTUATOR

CROSS REFERENCE TO RELATED APPLICATIONS

This application is a continuation of co-pending International Application No. PCT/DK02/00031; filed 16 Jan. 2002, the disclosure of which is incorporated herein by reference.

The present invention relates to a shape memory alloy actuator.

Shape memory alloy actuators utilizing the property of a wire made of shape memory alloys such as a nickel titanium alloy (commonly called nitinol) of contracting when heated past the transformation temperature are well known. The known actuators are all based on the contraction of the wire to directly provide the activating effect of the actuator. Hereby, the contraction speed and load capacity of the wire during transformation directly determines the speed and exerted force of the activating effect of the actuator.

For many uses it is desirable to attain an activating speed and force characteristic different from what can be achieved by directly utilizing the contraction of the shape memory alloy wire.

The main object of the invention is to provide a shape memory alloy actuator where the activating effect and force thereof is not directly dependent on the shape memory alloy wire incorporated in the actuator.

According to the invention, this object is obtained by the actuator comprising a body constituting or connected to an activating member such that said activating member is moved between a first and a second position when said body is moved between a third and a fourth position, releasable holding means for holding said body in said third position, at least one first and at least one second wire made of a shape memory alloy such as nitinol, said first wire being connected to said body such that shortening of the length of said first wire exerts a force on said body for moving same from said fourth to said third position, and a biasing means, such as a tension or compression spring or a piston and cylinder mechanism, attached to said body for biasing said body for moving same from said third to said fourth position, said second wire being arranged such relative to said holding means that shortening of the length of said second wire or wires releases said holding means allowing said biasing means to move said body from said third position to said fourth position.

Hereby the activating effect is determined directly by the characteristics and arrangement of the biasing means and not directly by the characteristics and arrangement of the shape memory wire incorporated.

Preferably, the actuator according to the invention further comprises means for intermittently directing an electric current through said first and second wires for heating same to at least the shape memory alloy transformation temperature. Hereby a particularly effective way of heating the wire is provided.

Advantageously, said holding means may comprise a brake mechanism and/or a pawl mechanism.

In the currently preferred embodiment of an actuator according the invention, said body is pivotably attached to a frame, said first and second wires are attached at one end thereof to said frame and connected at the other end thereof with said body such that shortening of the length of said first wire exerts a pivoting force on said body in one pivoting direction and shortening of the length of said second wire exerts a pivoting force on said body in the opposite pivoting direction, and said biasing means is attached to said frame and arranged for exerting a pivoting force on said body in at least one of said pivoting directions.

Hereby a particularly efficient way of establishing different types of holding means is obtained, one of said holding means being obtained by said biasing means being arranged for exerting a pivoting force on said body in both said pivoting directions with an intermediate balance point wherein said biasing means does not exert a pivoting force on said body.

The invention furthermore relates to a shape memory alloy actuator comprising:
  a frame with a body pivotably attached thereto,
  at least one first wire and at least one second wire made of a shape memory alloy such as nitinol attached at one end thereof to said frame and connected at the other end thereof with said body such that shortening of the length of said first wire exerts a pivoting force on said body in one pivoting direction and shortening of the length of said second wire exerts a pivoting force on said body in the opposite pivoting direction, and
  a biasing means attached to said frame and arranged for exerting a pivoting force on said body in at least one of said pivoting directions.

Advantageously, said biasing means may comprise a tension spring, a compression spring or a piston and cylinder mechanism, and the actuator may advantageously further comprise means for intermittently directing an electric current through said first and second wires for heating same to at least the shape memory alloy transformation temperature.

Furthermore, the invention relates to a shape memory alloy actuator comprising:
  a body with an activating member connected thereto such that said activating member is moved between a first and a second position when said body is moved between a third and a fourth position,
  holding means for holding said body in said third position,
  at least one first wire and at least one second wire made of a shape memory alloy such as nitinol, said first wire being connected to said body such that shortening of the length of said first wire exerts a force on said body for moving same from said fourth to said third position, and
  a biasing means, such as a tension or compression spring or a piston and cylinder mechanism attached to said body for biasing said body for moving same from said third to said fourth position,
  said second wire being arranged such relative to said holding means that shortening of the length of said second wire releases said body from said holding means such that said biasing means may move said body from said third position to said fourth position.

In the currently preferred embodiment of the actuator according to the invention, the body is pivotably attached to a frame, said first and second wires are attached at one end thereof to said frame and connected at the other end thereof with said body such that shortening of the length of said first wire exerts a pivoting force on said body in one pivoting direction and shortening of the length of said second wire exerts a pivoting force on said body in the opposite pivoting direction, and said biasing means is attached to said frame and arranged for exerting a pivoting force on said body in at least one of said pivoting directions.

Preferably, said biasing means is arranged for exerting a pivoting force on said body in both said pivoting directions with an intermediate balance point wherein said biasing means does not exert a pivoting force on said body.

Figure 2:
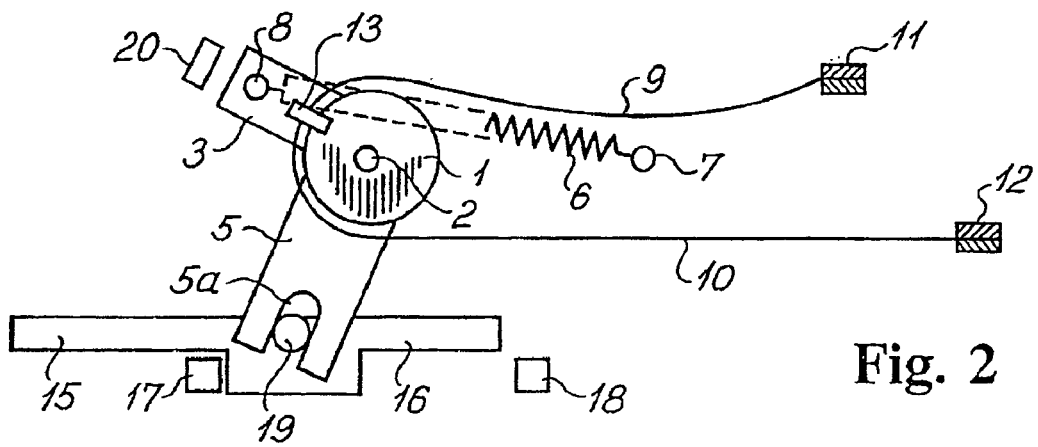
Figure 3:
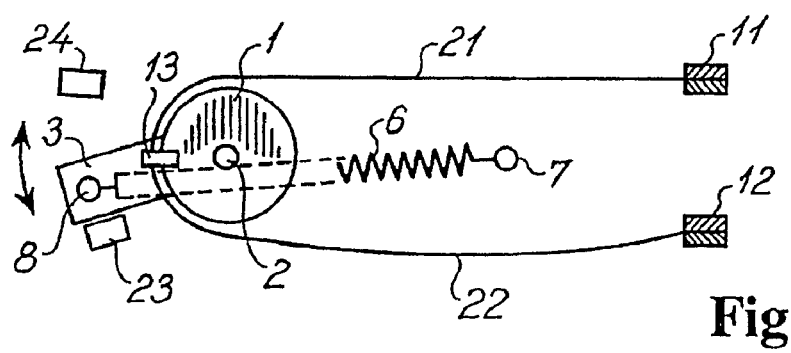
Figure 4:
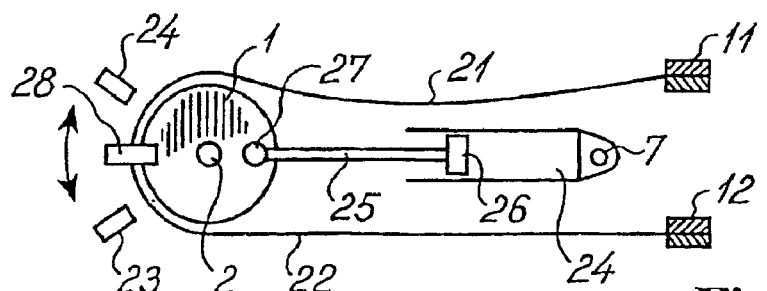

The invention will be described more in detail in the following with reference to various embodiments of a shape memory alloy actuator according to the invention shown, solely by way of example, in the accompanying drawings, where FIGS. 1 and 2 are schematic illustrations of a first embodiment of an actuator according to the invention in two different positions, namely with the activating pin fully retracted in FIG. 1, and with the activating pin fully extended in FIG. 2, FIGS. 3 and 4 are schematic illustrations of a second and third embodiment, respectively, of an actuator according to the invention, FIGS. 5 and 6 are perspective elevational views of the currently preferred embodiment (similar to the first embodiment shown in FIGS. 1 and 2) of an actuator according to the invention with the housing cover removed and the activating pin fully retracted in FIG. 5, and with the housing cover in place and the activating pin fully extended in FIG. 6, and FIGS. 7–9 are schematic illustrations of three further embodiments of an actuator according to the invention.

Referring now to FIGS. 1 and 2, a pivotable body in the form of a circular disc 1 is arranged for pivoting around a central pivot 2 fixedly attached to a not shown frame of the actuator, and the disc 1 is provided with a peripheral extension 3 and a yoke-like peripheral extension 5. A tension coil spring 6 is at one end thereof pivotably attached to a fastening pin 7 fixedly attached to said frame and is at the other end thereof pivotably attached to a fastening pin 8 fixedly attached to the peripheral extension 3.

Two wires or filaments 9 and 10 of a shape memory alloy such as nickel titanium alloy or nitinol, for instance supplied by the company DYNALLOY, INC, of Costa Mesa, Calif., USA, under the trade name FLEXINOL, are attached at one end thereof to electrically conductive terminals 11 and 12, respectively, fixedly attached to said frame.

The other end of each of the wires 9 and 10 is attached to an electrically conductive terminal 13 fixedly attached to the periphery of the disc 1. The wires 9 and 10 extend along the periphery of the disc 1 such that the wires 9 and 10 when tensioned extend along and are supported by said periphery. In the drawings the wires 9 and 10 are shown spaced from said periphery for the sake of clarity.

A sliding body 14 having two arms 15 and 16 is arranged for sliding movement between two stop pins 17 and 18 attached to the frame. A pin 19 attached to the sliding body 14 is received in the fork 5a of the yoke-like extension 5 such that the pin 19 may slide and rotate freely in the fork when the disc 1 pivots from the position shown in FIG. 1 to the position shown in FIG. 2 thereby slidingly displacing the body 14 from abutment against stop pin 18 to abutment against stop pin 17 with the arm 15, constituting the activating pin of the actuator, fully extended.

A proximity sensor 20 is attached to the frame and connected to not shown electrical conductors for transmitting a signal from the sensor to a not shown receiver. The terminals 11 and 12 are likewise each connected to an electrical conductor, not shown, connected to a not shown power source for supplying electrical power to the wires 9 and 10 for resistance heating thereof, the terminal 13 being likewise connected to the not shown power source through a not shown electrical conductor for closing the resistance heating circuit.

In use, the wires 9 and 10 are intermittently heated to the transformation or transition temperature (from martensitic to austenitic state) of the shape memory alloy which temperature for nitinol is approximately 90° C. Thereby the length of the wire is shortened. When the wire cools to below 90° C. the length thereof reverts to normal, i.e. the wire lengthens. The speed at which the shortening takes place, i.e. the contraction time, is directly related to the current input. i.e. the voltage applied over the terminals 11 or 12 and 13.

In the position depicted in FIG. 1, the disc 1 is in its outermost counter-clockwise position with the arm 15 fully retracted and with the wire 9 cooled to below 90° C. and the wire 10 heated to above 90° C. by applying an electrical voltage between the terminal 12 and 13 whereby an electrical current wil flow through the wire 10. The disc 1 has therefore been rotated counter-clockwise to the position shown by the contraction force exerted by the wire 10.

In the next step, the wire 10 is cooled to below 90° C. and thereby lengthens to the shape indicated by the dotted line 10a in FIG. 1. The actuator is now ready to perform an activating extension of the arm 15 towards the left, the end of the arm 15 being intended to come into contact with a not shown lever or button and depress or activate same during the movement of the arm 15 to the extended leftwards position thereof as depicted in FIG. 2.

Thereafter or simultaneously, the wire 9 is heated to above 90° C. whereby it contracts and exerts a clock-wise force on the disc 1 pivoting it clock-wise around the pivot 2 past the balance position of the disc 1 and spring 6 in which the attachment pins 7 and 8 of the spring 6 are aligned with the pivot 2.

When the disc 1 has rotated clock-wise past said balance point, the tension force exerted by the spring 7 will continue the clock-wise rotation of the disc 1 to the position shown in FIG. 2 with the arm 15 fully extended and the wire 9 slack though still above 90° C. This is the actual activating movement of the actuator where the force applied to the sliding body 14 by the extension 5 increases because of the increasing torque arm of the tension force exerted by the spring 6 on the disc 1.

For many applications where the force necessary to perform the function of the actuator, for instance depress a pump piston, increases during the activating stroke, said increase of the spring force torque arm as the disc 1 rotates is an advantageous feature.

Finally, the wire 10 is heated above 90° C. so that it contracts and pivots the disc 1 back to the position shown in FIG. 1 whereby the activating cycle is ready to be repeated.

The length of the wire 10 is larger than the length of the wire 9 because the contraction or shortening of the wire 10 must be large enough to pivot the disc 1 from the position shown i n FIG. 2 past the balance point mentioned above while the shortening of the wire 9 only has to be enough the pivot the disc 1 from the position shown in FIG. 1 past said balance point.

Nitinol wires will typically contract about 4%–4.5% when heated past the transition temperature. The uncontracted length of the wire 10 should be enough to ensure that the uncontracted wire is fully extended in the position shown in FIG. 2 and that the contracted wire 10 is fully extended when the disc 1 is at least slightly past said balance point in the counter-clockwise direction, i.e. the uncontracted length of wire 10 should be about 22–25 times the distance of travel of terminal 13 between the FIG. 2 position thereof and the balance point position thereof.

The necessary contraction force to be exerted by wires 9 and 10 are rather different because the contraction force of wire 9 only has to counteract the torque of the spring force of spring 6 with the relatively small torque arm in FIG. 1 while the contraction force of wire 10 has to counteract the considerably larger torque of said spring force in FIG. 2. The contraction force of a nitinol wire is larger the larger the diameter or cross sectional area of the wire. The cross sectional area of wire 10 is thus considerably larger than the cross sectional area of wire 9 or there may be a number of wires 10 with the same cross sectional area.

The latter possibility is chosen if it is necessary that the cooling-off time for the wires 10 is as short of possible so that the interval between the activating cycles may be as short as possible. Several small diameter wires with a certain total cross sectional area will cool more rapidly than a single larger diameter wire with the same cross sectional area.

The signal emitted by the proximity sensor 20 each time the extension 3 is in the position shown in FIG. 2 may be utilized for many different purposes such as for instance a mere monitoring of the correct function of the actuator or for controlling the timing of the heating of the wires 9 and 10 and thereby the timing of the activating stroke of the sliding body 14. Naturally, the location of the proximity sensor or of any other type of sensor for sensing the position of the disc 1 may be varied according to the purpose thereof, and several such sensors may be provided in different locations for instance for achieving a more complex control of the timing of the activating effect of the actuator.

Referring now to FIG. 3, this embodiment differs from the embodiment of FIGS. 1–2 in that a double activating effect may be achieved for each cycle of heating and cooling the shape memory wires 21 and 22 that in this case are of equal length and cross sectional area. The rotation of the disc 1 counter-clockwise and clockwise is limited by stop pins 23 and 24, respectively.

The activating member may be a sliding body similar to body 14 i n FIGS. 1–2 where both the arm 15 and the arm 16 perform an activating function, or the activating function may be a pull/push activation by for instance arm 15.

The disc 1 may alternatively be provided with a central torsion shaft projecting at right angles to the plane of the disc 1 as a prolongation of the pivot 2 such that the torsion shaft functions as the activating member by for instance rotating a lever to and fro. Many different types of activating members connected to the disc 1 will be obvious to those skilled in the art.

In the position shown in FIG. 3, the disc 1 has just performed an activating rotation counter-clockwise under the influence of the counter-clockwise torque of the force of the spring 6 and is ready for the initiation of a rotation clockwise by heating the wire 21 so that the disc 1 is rotated against the counter-clockwise torque of the spring force until the balance point is passed. Then the activating rotation clockwise is performed by the clockwise torque of the spring force.

Referring now to FIG. 4, the terminal 13 of the embodiments of FIGS. 1–3 has been substituted by a combined terminal and abutment member 28 for abutting the stop pins 24 and 25. Furthermore, another type of biasing means is utilized, namely a piston and cylinder mechanism comprising a pressurized cylinder 24 pivotably attached to pin 7, a piston 26 and a piston rod 27 pivotably attached to the disc 1 by means of a pin 27.

The piston and cylinder mechanism 24–25 functions like a compression spring and could in fact be substituted by a compression spring. In FIG. 4 the disc 1 is in the balance point position where the pin 7, the pin 27 and the pivot 2 are aligned such that the pressure exerted on the disc 1 by the piston rod 25 does not produce any torque on the disc 1. In the situation shown in FIG. 4, the wire 22 is contracting and rotating the disc counter-clockwise past the balance point. As soon as the balance point has been passed, the torque from the piston rod 25 will cause the activating counter-clockwise rotation of the disc 1 until the member 28 abuts the stop pin 23 whereupon a clockwise rotation may be initiated in a manner very similar to that described above in relation to FIG. 3.

Obviously, the tension spring 6 in FIGS. 1–2 could also be substituted by a piston and cylinder mechanism or a compression spring in an arrangement similar to FIG. 4.

Referring now to FIGS. 5–6, the currently preferred embodiment of an actuator according to the invention is very similar to the embodiment schematically shown in FIGS. 1–2. All elements common to the embodiments of FIGS. 1–2 and FIGS. 5–6 are referenced by the same numerals.

The disc 1 and sliding body 14 are enclosed in a housing 30 having a cover 31 in which a slit 32 is provided for allowing free movement of the pin 8 extending through the slit 32.

Electrical conductors 33, 34 and 35 are connected to terminals 13, 11 and 12, respectively, for supplying electrical current from a not shown battery for resistance heating of the nitinol wires 9 and 10 to the transformation temperature of about 90° C. Electrical conductors 36 connect the proximity sensor 20 to a not shown receiver for transmitting signals thereto.

The position shown in FIG. 5 corresponds to the position shown in FIG. 1, while FIG. 6 correspond to FIG. 2. As regards the operation of the actuator, reference is made to the description thereof above in connection with FIGS. 1–2.

The actuator of FIGS. 5–6 is well suited for depressing the piston of a pump, for instance a medical infusion pump, by means of the arm 15. In connection with such use with an infusion pump, eight FLEXINOL wires with a diameter of 0.002 Inches are used as the wires 9 while two of the same wires are used as wires 10. The cooling of the wires 9 and 10 takes place by natural radiation and convection, and the current input for heating the wires is chosen such that the actuator may activate the pump several times per second. An additional coil tension spring 6 may be arranged on the other side of the housing attached to a prolongation of the same pins 8 and 7 as used for the visible spring 6. As regards the characteristics of the FLEXINOL wires, reference is made to the relevant publications from DYNALLOY, INC, which are readily available.

Figure 7:
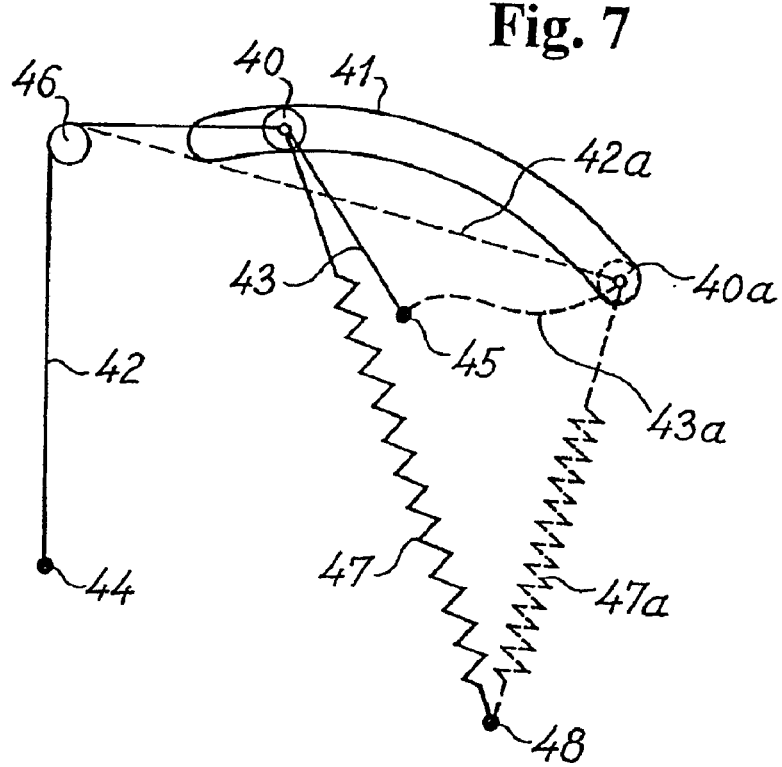

Referring now to FIG. 7, a body 40 is arranged for movement in a track 41, the body 40 being connected with a not shown activating member. Shape memory alloy wires 42 and 43 are attached to a not shown frame at 44 and 45, respectively, and to the body 40, the wire 42 extending around a pin or pulley 46 attached to said frame. A tension spring 47 is attached to the frame at 48 and to the body 40. The wires 42 and 43 are connected to electrical terminals at 44, 45 and 40 for being supplied with electrical resistance heating current as described above with respect to FIGS. 1–6.

When the body 40 is in the extreme left position in the track 41, the geometry of the track 41 relative to the corresponding angle of the spring 47 will entail that the spring 47 cannot move the body 40 in the track. When the wire 43 is heated, the contraction thereof will, together with the force from the spring 47 move the body to the position shown in FIG. 7 which is past the balance point whereby the force of the spring 47 is enough to continue moving the body towards the right in the track 41. The shape and orientation of the leftmost portion of the track 41 thus functions as a holding means for holding the body in the position in the said leftmost portion of the track 41. Thus, the contraction of the wire 45 releases the body 41 from the thus defined holding means such that the spring 47 can move the body to the rightmost extremity of the track 41 indicated by dotted lines 40a with the corresponding position of the two wires and the spring being indicated by the dotted lines 42a, 43a and 47a.

Subsequent contraction of the wire 42a will move the body from the position 40a towards the left, thereby "cocking" the spring 47 when the body has passed said balance point. The activating stroke of the actuator takes place when the spring is released from the "cocked" condition and moves the body 41 to the right in the track 41.

Figure 8:
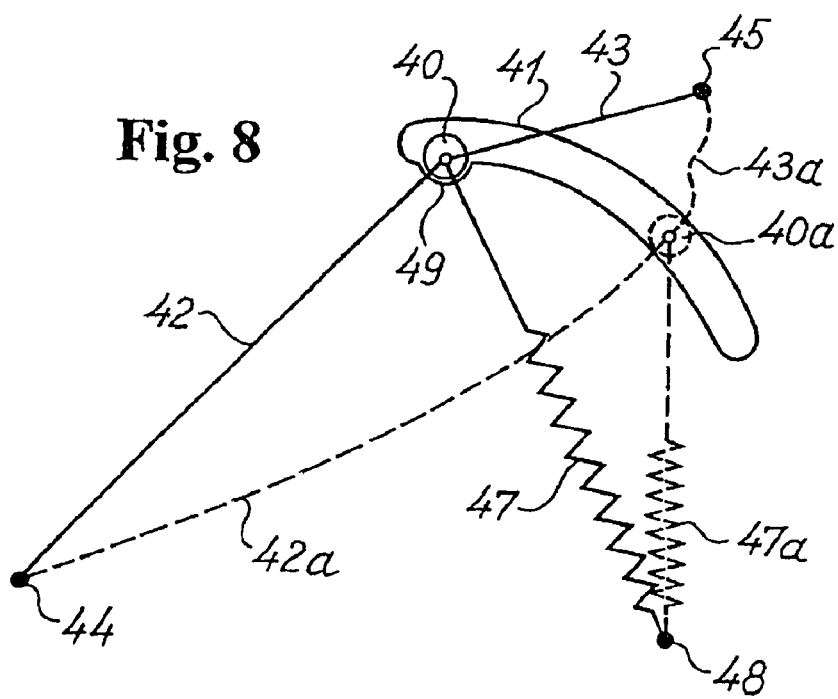

Referring now to FIG. 8, basically the same arrangement as in FIG. 7 has been utilized except that the leftmost portion of the track 41 for holding the body 40 with the spring 47 "cocked" has been eliminated and substituted by a depression 49 in the track with a depth sufficient to prevent the spring force from moving the body to the right until being assisted by contraction of the wire 43.

Instead of the depression 49 in FIG. 8, a friction brake could be installed in the track 41 for instance by slightly reducing the width of the track. Hereby the holding means for holding the body 40 and "cocking" the spring 47 would be the friction brake.

Figure 9:
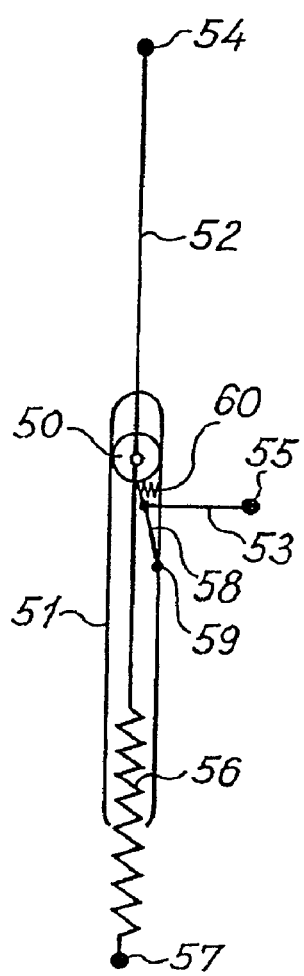

In the embodiment shown in FIG. 9, a body 50 is arranged for displacement in a track 51 and shape memory alloy wires 52 and 53 are attached to pins 54 and 55, respectively, the wire 52 being also attached to the body 50. A tension spring 56 is attached to pin 57 and the body 50.

A pawl 58 pivotably attached at 59 to the inner surface of the track 51 is biased towards the inside of the track by a compression spring 60 and the pawl 58 is attached to the wire 53 such that shortening of the wire 53 will pull the pawl 58 toward the inner surface of the track against the bias of the compression spring 60.

In the position shown in FIG. 9, the wire 52 has been heated so as to contract and pull the body past the pawl 58 by compressing the spring 60. In this position the spring 56 is "cocked" and the body 50 is held in this position by the holding means constituted by the pawl 58.

Subsequently, the wire 52 is cooled for lengthening thereof and the wire 53 is heated for shortening thereof such that the pawl 58 is pivoted to a position flush with the inner surface of the track 51. Hereby the body 50 is released and may be pulled by the tension force of the spring 56 to achieve an activating motion of the body downwards as seen in FIG. 9

It will be obvious to those skilled in the art that a pawl mechanism similar to the one described in connection with FIG. 9 may be employed with the other embodiments shown in FIGS. 1–2 and FIG. 8 by utilizing the wires 9 and 43, respectively, to release a corresponding pawl mechanism instead of as described and shown.

In broad terms, the basic idea of the invention could be said to be to combine influencing a body (that constitutes or is connected to an activating member) with a biasing means and two shape memory alloy wires, contraction of one wire causing the body to move against the influence of the biasing means, thereby, so to say, "cocking" (tensioning or compressing) said biasing means, and contraction of the other wire causing the body to move under the influence of the biasing means by releasing at least part of said tension or compression of the biasing means achieved by said "cocking" thereof.

It will be obvious to those skilled in the art that many variations of the shown embodiments are conceivable for the application of the above basic inventive idea.

An actuator according to the invention may be used inter alia for a great variety of pushing and/or pulling actions, rotating actions, for locking bolts in car doors, hospital beds etc, for release trigger mechanisms for instance for cash registers, for signal arms for toy railroads, for robots for instance for picking up or sorting objects, for opening and closing valves and so on.

What is claimed is:

1. A shape memory alloy actuator comprising:
    a body having an activating member such that said activating member is moved between a first and a second position when said body is moved between a third and a fourth position,
    holding means for holding said body in said third position, said holding means comprising a pawl mechanism,
    at least one first wire and at least one second wire made of a shape memory alloy, said first wire being connected to said body such that shortening of the length of said first wire exerts a force on said body for moving same from said fourth to said third position, and
    a biasing means, selected from the group consisting of at least one of a compression spring, a tension spring, and a piston and cylinder mechanism attached to said body for biasing said body for moving same from said third to said fourth position,
    said second wire being arranged such relative to said holding means so that shortening of the length of said second wire releases said body from said holding means such that said biasing means may move said body from said third position to said fourth position.

2. An actuator according to claim 1 and further comprising means for intermittently directing an electric current through said first and second wires for heating same to at least the shape memory alloy transformation temperature.

3. An actuator according to claim 1, wherein said holding means further comprises a brake mechanism.

4. An actuator according to claim 1, wherein said body is pivotably attached to a frame, said first and second wires are attached at one end thereof to said frame and connected at the other end thereof with said body such that shortening of the length of said first wire exerts a pivoting force on said body in one pivoting direction and shortening of the length of said second wire exerts a pivoting force on said body in the opposite pivoting direction, and said biasing means is attached to said frame and arranged for exerting a pivoting force on said body in at least one of said pivoting directions.

5. An actuator according to claim 4, wherein said biasing means is arranged for exerting a pivoting force on said body in both said pivoting directions with an intermediate balance point wherein said biasing means does not exert a pivoting force on said body.

6. A shape memory alloy actuator comprising:
    a body having an activating member such that said activating member is moved between a first and a second position when said body is moved between a third and a fourth position,
    releasable holding means for holding said body in said third position, said holding means comprising a pawl mechanism,
    at least one first and at least one second wire made of a shape memory alloy, said first wire being connected to said body such that shortening of the length of said first wire exerts a force on said body for moving same from said fourth to said third position, and
    a biasing means, selected from the group consisting of one or more of a tension spring, a compression spring, and a piston and cylinder mechanism, attached to said body for biasing said body for moving same from said third to said fourth position, said at least one second wire being arranged such relative to said holding means that shortening of the length of said second wire releases said holding means allowing said biasing means to move said body from said third position to said fourth position.

7. An actuator according to claim 6 and further comprising means for intermittently directing an electric current through said first and second wires for heating same to at least the shape memory alloy transformation temperature.

8. An actuator according to claim 6, wherein said holding means further comprises a brake mechanism.

9. An actuator according to claim 6, wherein said body is pivotably attached to a frame, said first and second wires are attached at one end thereof to said frame and connected at the other end thereof with said body such that shortening of the length of said first wire exerts a pivoting force on said body in one pivotaing direction and shortening of the length of said second wire exerts a pivoting force on said body in the opposite pivoting direction, and said biasing means is attached to said frame and arranged for exerting a pivoting force on said body in at least one of said pivoting directions.

10. An actuator according to claim 9, wherein said biasing means is arranged for exerting a pivoting force on said body in both said pivoting directions with an intermediate balance point wherein said biasing means does not exert a pivoting force on said body.

* * * * *